United States Patent
Erez et al.

(10) Patent No.: US 6,908,915 B1
(45) Date of Patent: Jun. 21, 2005

(54) TRICYCLIC COMPOUNDS AND THEIR USES AS ANTIARRHYTHMIC ANTIFIBRILLATORY AND DEFIBRILLATORY AGENTS

(75) Inventors: Mordechai Erez, Tel Aviv (IL); Ofra Levy, Petach Tikva (IL); Ehud Keinan, Timrat (IL)

(73) Assignee: Technion Research & Development Foundation Ltd., Haifa (IL)

( * ) Notice: Subject to any disclaimer, the term of this patent is extended or adjusted under 35 U.S.C. 154(b) by 120 days.

(21) Appl. No.: 10/069,455

(22) PCT Filed: Aug. 27, 2000

(86) PCT No.: PCT/IL00/00510

§ 371 (c)(1),
(2), (4) Date: Jul. 8, 2002

(87) PCT Pub. No.: WO01/15656

PCT Pub. Date: Mar. 8, 2001

(51) Int. Cl.⁷ .................... C07D 223/22; C07D 223/28; A61K 31/55; A61K 31/5513; A61P 9/06

(52) U.S. Cl. ...................... 514/217; 514/220; 540/558; 540/590; 540/591; 540/592

(58) Field of Search ................................. 514/217, 220; 540/588, 590; 544/588, 590, 591, 592

(56) References Cited

U.S. PATENT DOCUMENTS

| | | | | |
|---|---|---|---|---|
| 2,976,281 A | * | 3/1961 | Schindler et al. | 540/591 |
| 3,335,133 A | * | 8/1967 | Kaiser et al. | 540/588 |
| 3,842,091 A | * | 10/1974 | Kawashima et al. | 540/576 |
| 4,495,281 A | * | 1/1985 | Buckler et al. | 436/537 |
| 4,668,640 A | * | 5/1987 | Wang et al. | 436/536 |
| 5,002,943 A | | 3/1991 | Mihm et al. | |
| 5,066,426 A | | 11/1991 | Wang et al. | |
| 5,264,432 A | | 11/1993 | Rüger et al. | |

FOREIGN PATENT DOCUMENTS

EP          0515796          12/1992

OTHER PUBLICATIONS

Lin, John W. P. Journal of Polymer Science, Polymer Chemistry Edition, 17(12), 3797–810 (English) 1979.*
Gozlan, Igal; Halpern, Marc; Rabinovitz, Mordecai; Avnir, David; Ladkani, David, lJournal of Heterocyclic Chemistry, 19(6), 1569–71 (English) 1982.*
Olshausen et al, "Sudden Cardiac Death While Wearing Holter Monitor", *Am J Cardiol*, 67(5):381–386, 1991 (Abstract).
Williams, V., "Classifying Antiarrhythmic Actions: By Facts or Speculation", *J Clin Pharmacol*, 32(11):964–977, 1992 (Abstract).
(No author listed) "Preliminary Report: Effect of Encainde and Flecainide on Mortality in a Ransomized Trial of arrhythmia Suppression after Myocardial Infarction. Cardia Arrhythmia Suppression Trail (CAST) Investigators", *N. Engl J Med*, 321(6):406–412, 1989 (Abstract).
Manoach et al, "Spontaneous Termination of Electrically Induced Ventricular Fibrillation", Progress in Electrocardiology, Glasgow, Ed. P. MacFarlane. Pitman Medical, pp 361–365, 1979.
Manoach et al, "Spantaneous Termination and Initiation of Ventricular Fibrillation as a Function of Heart Size, Age, Autonomic Autoregulation, and drugs: A Comparative Study on Different Species of Different Age", *Heart Vessels*, Suppl.2:56–68, 1987.
Manoach et al, "Reduction of Infarct Size Following Acute Coronary Occlusion by Augmenting Collateral Blood Supply Induced by Infusion of Tricyclic Antidepressants", *Heart Vessels*, 3:80–83, 1987.
Manoach et al, "The Cardio–Protective Features of Tricyclic Antidepressants", *Gen. Pharmac.*, 20(3):269–275, 1989.
Manoach et al, "Propertis Required for Self–Ventricular Defibrillation: Influence of Age and Drugs", *Cardiology in the Elderly*, 1:337–344, 1993.
Manoach et al, "The Role of Catecholamines on Intercellular Coupling, Myocardial Cell Synchronization and Self Ventricular Defibrillation", *Molecular and Cellular Biochemistry*, 147:181–185, 1995.
Erez et al, "Dibenzazepines and Phenothiazines—A Winding Path to Defibrillatory Antiarrhythmic Agents", *Exp. Clin. Cardiol.*, 2(1):59–63, 1997.
Kaverina et al, "New Cardiovascular Drugs among Phenothiazine Derivitives and Related Tricyclic Systems", *Sov. Med. Rev. A. Cardiology*, 3:81–100, 1991.

* cited by examiner

Primary Examiner—Thomas C. McKenzie

(74) Attorney, Agent, or Firm—G. E. Ehrlich (1995) Ltd.

(57) ABSTRACT

A compound having a general formula (II) wherein $R_1$ is saturated or unsaturated alkyl, amino-alcohol, diamino, cycloalkyl, and $C(=O)(CH_2)_n NR'R''$, $(CH_2)_n CHOHCH_2 NR'R''$, wherein n is an integer, $R_{Q,RT}$, R', and R" are each independently a hydrogen, halogen, hydroxyl, saturated, unsaturated, aliphatic, or branched alkyl, substituted or unsubstituted $(CH_2)_m$-(hetero)aryl, and sulfonylamide; q and r are each an integer independently selected from 1–4; and pharmaceutically acceptable salts thereof, and the new therapeutic uses thereof and similar compounds as defibrillating, and/or anti-fibrillatory, and/or anti-arrhythmic and/or anti-ischemic drugs.

(II)

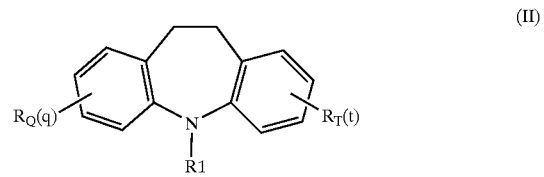

43 Claims, No Drawings

TRICYCLIC COMPOUNDS AND THEIR USES AS ANTIARRHYTHMIC ANTIFIBRILLATORY AND DEFIBRILLATORY AGENTS

FIELD AND BACKGROUND OF THE INVENTION

The present invention relates to tricyclic compounds of the 11-oxo-dibenzodiazepin and dibenzoazepin families, and their new therapeutic uses as defibrillating, and/or anti-fibrillatory, and/or anti-arrhythmic and/or anti-ischemic drugs. More particularly, the present invention relates to 5(N-acyl)-derivatives and 5(N-β-aminoalcohol)-derivatives of 11-oxo-10,11-dihydro-dibenzo[b,e] [1,4]diazepin and 10,11-dihydro-dibenzo[b,f]azepin, compositions including same, methods of their synthesis, purification and formulation and their use in prevention and treatment of cardiac disorders, such as, but not limited to, arrhythmia and ventricular fibrillation.

Sudden cardiac death is a leading cause of mortality, and ventricular fibrillation (VF) is thought to play a major role in sudden cardiac death [1]. Ventricular fibrillation can be divided into two categories: sustained VF (SVF), which is fatal, unless external defibrillating intervention is practiced, or transient VF (TVF), which terminates spontaneously. Currently, only one effective approach has been found to terminate SVF once SVF is initiated, which is the application of electrical defibrillation. Electrical defibrillation can be applied either externally or internally, by implantation. However, this approach has a number of disadvantages. For example, electrical defibrillation must be applied immediately to be effective, yet may not be sufficient, and may even cause damage. In addition, an implanted defibrillator requires invasive treatment. Thus, artificial defibrillation is not a cure, and does not prevent reoccurrence of VF.

Antiarrhythmic drugs constitute an alternative, preferable approach, as they are aimed at preventing initiation of VF by decreasing the incidence of ventricular arrhythmias that can lead to VF [2]. In addition, certain drugs, such as bretylium, have been shown to transform SVF into TVF [3]. The effectiveness of this treatment, however, is limited, since various mechanisms can be involved in the initiation of VF, such that antiarrhythmic drugs are unlikely to absolutely eliminate arrhythmias and totally prevent VF initiation. Furthermore, recent surveys (such as the Cardiac Arrhythmia Suppression Trial, CAST, II and I [4,5], have clearly shown limitations to this approach. Thus, a new cardiac protective therapy is needed. For this reason, a new approach has been proposed, to use a new class of antiarrhythmic drugs [6], which can enhance spontaneous termination of VF, once it occurs. In several animal species, and even, though rarely, in humans, VF can revert spontaneously into sinus rhythm, resulting in the non-fatal TVF. It has been previously found that several factors contribute to the ability to self-defibrillate. For example, self-defibrillation is a normal feature of young mammals, but this ability decreases with age [7]. Such spontaneous defibrillation requires a relatively high degree of intercellular synchronization [8], and is enhanced by increased sympathetic activity. Thus, treatments with compounds that elevate extraneuronal catecholamine levels in the heart enhance self-defibrillation and administration of β-adrenergic blockers abolishes this activity [9].

In order to design and synthesize new, more potent and selective defibrillatory drugs, it has been found that certain dibenzoazepins (imipramine, desipramine, maprotiline and bonnecore) and phenothiazins (chlopromazin, moricizine and trifluoperazin), induce self-defibrillation and increase the threshold for electrical fibrillation [10, 11]. Moreover, tricyclic antidepressants, in addition to their antiarrhythmic and defibrillating effects, have the ability to decrease the ischemic area in the heart following coronary occlusion [12]. However, these cardio-protective effects of the compounds were expressed when relatively high doses were used, resulting in a low therapeutic index.

There is thus a need for, and it would be useful to have, pharmaceutically effective compounds which are safe and useful for the treatment of ventricular fibrillation, particularly for the induction of TVF once SVF has been initiated, and for both treating and preventing pathological conditions associated with VF.

SUMMARY OF THE INVENTION

The present invention relates to 5(N-acyl)-derivatives and 5(N-β-aminoalcohol)-derivatives of 11-Oxo-10,11-dihydro-dibenzo [b,e][1,4] diazepin and 10,11-dihydro-dibenzo[b,f] azepin, compositions including same, methods of their synthesis, purification and formulation and their use in prevention and treatment of cardiac disorders. It is shown herein for the first time that these new tricyclic compounds and some previously known tricyclic compounds have been synthesized and have been shown to have substantial activity as chemical defibrillating agents.

According to the present invention, there is provided a compound having a general formula (I):

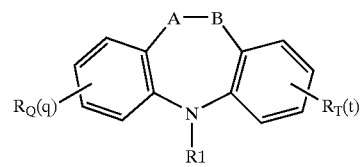

wherein A is CH, $CR_2R_3$ or C=O; B is CH, $CR_4R_5$ or $NR_6$, wherein $R_2$, $R_3$, $R_4$, $R_5$ and $R_6$ are each independently selected from the group consisting of hydrogen, halogen, hydroxyl, saturated, unsaturated, aliphatic, or branched alkyl, substituted or unsubstituted $(CH_2)_m$-(hetero)aryl; or A and B together are C=C; $R_1$ is saturated or unsaturated alkyl, ammo-alcohol, diamino, cycloalkyl, and C(=O) $(CH_2)_m$NR'R", $(CH_2)_n$C*HOHCH$_2$NR'R" (the chiral C, which is marked by * can be the R anantiomer, the S anatiomer, be in a racemic mixture or in any other ratio between the R and S anantiomers), wherein n is an integer; $R_Q$, $R_T$, R', and R" are each independently a hydrogen, halogen, hydroxyl, saturated, unsaturated, aliphatic, or branched alkyl, substituted or unsubstituted $(CH_2)_m$-(hetero) aryl, and sulfonylamide; q and t are each an integer independently selected from 1–4; and pharmaceutically acceptable salts thereof.

Preferably, $R_1$ is selected from the group consisting of β-amino-alcohol, C(=O)(CH$_2$)$_n$NR'R" and $(CH_2)_n$CHOHCH$_2$NR'R" wherein n is an integer and further wherein the chiral carbon atom can be the R or S anantiomer, a racemic mixture thereof or a mixture of any ratio thereof; and R', R" are each independently selected from the group consisting of hydrogen, halogen, hydroxyl, saturated, unsaturated, aliphatic, or branched alkyl; and pharmaceutically acceptable salts thereof. Examples of suitable alkyl moieties include but are not limited to iso-propyl, iso-butyl, tertbutyl and sec-butyl. Most preferably, R" is iso-propyl.

According to a preferred embodiment of the present invention, A and B are each an alkyl chain, more preferably a CH moiety, $R_2$, $R_3$, $R_4$ and $R_5$ are each hydrogen, and $R_1$ is $C(=O)(CH_2)_n NR'R''$ and $(CH_2)_n CHOHCH_2 NR'R''$, n being 0–5. Preferably, R and R' are each hydrogen and R" is selected from the group consisting of methyl, ethyl, propyl, iso-propyl, n-butyl, sec-butyl, iso-butyl and tert-butyl.

According to a preferred embodiment of the present invention A is $CR_2R_3$ or $C=O$ and B is $CR_4R_5$; R, $R_2$, $R_3$, $R_4$, $R_5$ and $R_6$ are each a hydrogen, and $R_1$ is $C(=O)(CH_2)_n NR'R''$ and $(CH_2)_n CHOHCH_2 NR'R''$, n being 0–5.

DESCRIPTION OF THE PREFERRED EMBODIMENTS

The present invention relates to a group of compounds, based upon the general backbone structure of tricyclic antidepressants, namely, 11-oxo-dibenzodiazepins and dibenzoazepins N-substituted at the 5 position, as well as to pharmaceutical compositions of these compounds and to their use in the treatment and prevention of ventricular fibrillation and ischemic damage by local or systemic application. More specifically, these compounds are demonstrated to have a defibrillating effect on ventricular fibrillation, once it actually occurs.

Previous studies, aimed at characterizing the structure-activity relationships of dibenzoazepins and phenothiazines accountable to improved defibrillating activity, have indicated the relevance of several structural features of the backbone of these molecules for their efficacy against ventricular fibrillation. First, activity of the tricyclic compounds correlated with higher (more bent) dihedral angle between the two benzo rings in the tricyclic skeleton. This angle is also considered to play a detrimental role in the type of central nervous system activity of these compounds, as well as their different selectivity towards catecholamine reuptake systems (such as noradrenaline, serotonine and dopamine). Second, compounds with 5-N-substituted secondary aminoalkyl side chains (such as desipramine) exhibit higher defibrillatory activity, as opposed to tertiary alkylamine (such as in imipramine) and lastly, transition from aminoalkyl to aminoacyl in the side chain at position 10 of the phenothiazine tricyclic nucleus results in an increase in antiarrhythmic activity and decrease in psychotropic activity [10].

The development of the disclosed class of tricyclic compounds was based on the rationalized design of new compounds, aimed at more focused and selective activity as chemical defibrillators, as well as identifying additional molecules which are able to overcome shortcomings of the presently utilized approaches (electrical defibrillation, antiarrhythmic drugs, described above), and which are able to convert the fatal sustained ventricular fibrillation to the non-fatal transient one.

The experiments described below in the Examples section demonstrate that the disclosed compounds are indeed effective in transforming the potentially fatal VF type, SVF, to the spontaneously-defibrillating type, TVF. In addition, the preferred structure is indicated in terms of a structure-activity-relationship, indicating the importance of certain structural elements in obtaining potent, selective therapeutic activity, and minimizing untoward side effects. Thus, a compound according to the present invention includes derivatives of 5-(N-alkyl), 5-(N-acyl) and 5-(N-β-aminoalcohol) dibenzoazepins of the general formula (II):

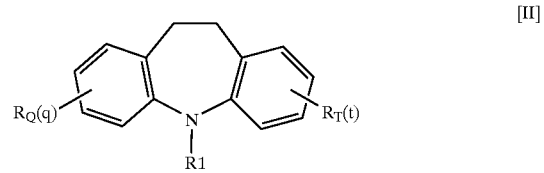

[II]

wherein $R_1$ is saturated or unsaturated alkyl, amino-alcohol, diamino, cycloalkyl, $C(=O)(CH_2)_n NR'R''$ or $(CH_2)_n CHOHCH_2 NR'R''$, wherein n is an integer; $R_Q$, $R_T$, R', and R" are each independently a hydrogen, halogen, hydroxyl, saturated, unsaturated, aliphatic, or branched alkyl, substituted or unsubstituted $(CH_2)_m$-(hetero)aryl, and sulfonylamide; q and t are each an integer independently selected from 1–4; and pharmaceutically acceptable salts thereof.

Preferably, $R_1$ is selected from the group consisting of β-amino-alcohol, $C(=O)(CH_2)_n NR'R''$, and $(CH_2)_n CHOHCH_2 NR'R''$ wherein n is an integer and R', R" are each independently selected from the group consisting of hydrogen, halogen, hydroxyl, saturated, unsaturated, aliphatic, or branched alkyl; and pharmaceutically acceptable salts thereof. Examples of suitable alkyl moieties include but are not limited to iso-propyl, iso-butyl, tert-butyl and sec-butyl. Most preferably, R" is iso-propyl. Also most preferably, $R_Q$ and $R_T$ are each a hydrogen, and q and t are each 4.

The compounds of the present invention are also useful as an active ingredient in a composition for treating or preventing a cardiac disorder, such as ventricular fibrillation, featuring a pharmaceutically effective amount of a tricyclic compound in combination with a pharmaceutically acceptable carrier, in which the tricyclic compound is of a general formula (I):

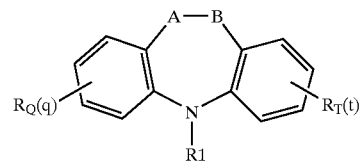

wherein A is CH, $CR_2R_3$ or $C=O$; B is CH, $CR_4R_5$ or $NR_6$, wherein $R_2$, $R_3$, $R_4$, $R_5$ and $R_6$ are each independently selected from the group consisting of hydrogen, halogen, hydroxyl, saturated, unsaturated, aliphatic, or branched alkyl, substituted or unsubstituted $(CH_2)_m$-(hetero)aryl; or A and B together are $C=C$; $R_1$ is saturated or unsaturated alkyl, amino-alcohol, diamino, cycloalkyl, and $C(=O)(CH_2)_n NR'R''$, $(CH_2)_n CHOHCH_2 NR'R''$, wherein n is an integer; $R_Q$, $R_T$, R', and R" are each independently a hydrogen, halogen, hydroxyl, saturated, unsaturated, aliphatic, or branched alkyl, substituted or unsubstituted $(CH_2)_m$-(hetero)aryl, and sulfonylamide; q and t are each an integer independently selected from 1–4; and pharmaceutically acceptable salts thereof.

Preferably, $R_1$ is selected from the group consisting of β-amino-alcohol, $C(=O)(CH_2)_n NR'R''$, and $(CH_2)_n CHOHCH_2 NR'R''$ wherein n is an integer and R', R" are each independently selected from the group consisting of hydrogen, halogen, hydroxyl, saturated, unsaturated, aliphatic, or branched alkyl; and pharmaceutically acceptable salts thereof. Examples of suitable alkyl moieties include but are not limited to iso-propyl, iso-butyl, tert-butyl and sec-butyl. Most preferably, R" is iso-propyl.

According to a preferred embodiment of the present invention, A and B are each an alkyl chain, more preferably a CH moiety, $R_2$, $R_3$, $R_4$ and $R_5$ are each hydrogen, and $R_1$ is $C(=O)(CH_2)_n NR'R''$ and $(CH_2)_n CHOHCH_2 NR'R''$, n being 0–5. Preferably, R and R' are each hydrogen and R'' is selected from the group consisting of methyl, ethyl, propyl, iso-propyl, n-butyl, sec-butyl, iso-butyl and tert-butyl.

According to a preferred embodiment of the present invention A is $CR_2R_3$, or C=O and B is $CR_4R_5$, R, $R_2$, $R_3$, $R_4$, $R_5$ and $R_6$ are each a hydrogen, and $R_1$ is $C(=O)(CH_2)_n NR'R''$ and $(CH_2)_n CHOHCH_2 NR'R''$, n being 0–5. More preferably, n is 1 or 2.

Hereinafter, the term "tricyclic compound" refers to 5-(N-acyl) or 5-(N-alkylβaminoalcohol)-derivatives or 5-(N-alkyl)-derivatives of 10,11-dihydro-dibenzo[b,f]azepin or 5-(N-acyl) or 5-(N-alkylβaminoalcohol)-derivatives or 5-(N-alkyl)-derivatives of 11-Oxo-10,11-dihydro-dibenzo[b,e][1,4] diazepin compounds of the present invention.

Hereinafter, the term "derivative" refers to the result of a chemically altering, modifying or changing a molecule or a portion thereof, such that the molecule either maintains or increases its functionality.

Hereinafter, the term "pharmaceutically acceptable carrier" refers to a carrier or a diluent that does not cause significant irritation to an organism and does not abrogate the biological activity and properties of the administered compound.

Hereinafter, the term "pharmaceutically effective amount" refers to that amount of the compound being administered which will relieve to some extent one or more of the symptoms of the disorder being treated.

The composition of the present invention may be optionally and preferably designed for topical application such as a slow release or transdermal patch of the tricyclic compound. The composition for slow release includes particles including a slow release carrier (typically, a polymeric carrier), and the tricyclic compound. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein.

Specifically, a slow release formulation or a transdermal patch of the tricyclic compound can be used in patients prone to cardiac disorders, such as arrhythmias, or with a known history of arrhythmic or fibrillatory episodes.

One particularly preferred embodiment of the present invention is parenteral administration of the tricyclic compound, for example intravenously. Further according to the present invention there is provided a method for treating or preventing a cardiac disorder, such as ventricular fibrillation, in a subject, by administering a pharmaceutically effective amount of a tricyclic compound of a general formula (I):

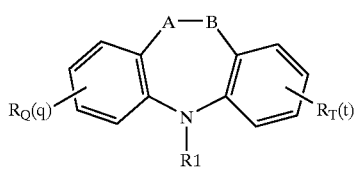

wherein A is CH, $CR_2R_3$ or C=O; B is CH, $CR_4R_5$ or $NR_6$, wherein $R_2$, $R_3$, R4, $R_5$ and $R_6$ are each independently selected from the group consisting of hydrogen, halogen, hydroxyl, saturated, unsaturated, aliphatic, or branched alkyl, substituted or unsubstituted $(CH_2)_m$-(hetero)aryl; or A and B together are C=C; $R_1$ is saturated or unsaturated alkyl, amino-alcohol, diamino, cycloalkyl, and C(=O) $(CH_2)_n NR'R''$, $(CH_2)_n CHOHCH_2 NR'R''$, wherein n is an integer; $R_{Q, RT}$, R', and R'' are each independently a hydrogen, halogen, hydroxyl, saturated, unsaturated, aliphatic, or branched alkyl, substituted or unsubstituted $(CH_2)_m$-(hetero)aryl, and sulfonylamide; q and t are each an integer independently selected from 1–4; and pharmaceutically acceptable salts thereof.

Preferably, $R_1$ is selected from the group consisting of β-amino-alcohol, $C(=O)(CH_2)_n NR'R''$, and $(CH_2)_n CHOHCH_2 NR'R''$ wherein n is an integer and R', R'' are each independently selected from the group consisting of hydrogen, halogen, hydroxyl, saturated, unsaturated, aliphatic, or branched alkyl; and pharmaceutically acceptable salts thereof. Examples of suitable alkyl moieties include but are not limited to iso-propyl, iso-butyl, tertbutyl and sec-butyl. Most preferably, R'' is iso-propyl.

According to a preferred embodiment of the present invention, A and B are each an alkyl chain, more preferably a CH moiety, $R_2$, $R_3$, $R_4$ and $R_5$ are each hydrogen, and $R_1$ is $C(=O)(CH_2)_n NR'R''$ and $(CH_2)_n CHOHCH_2 NR'R''$, n being 0–5. Preferably, n is 1 or 2. Preferably, R and R' are each hydrogen and R'' is selected from the group consisting of methyl, ethyl, propyl, iso-propyl, n-butyl, sec-butyl, iso-butyl and tert-butyl.

According to a preferred embodiment of the present invention A is $CR_2R_3$ or C=O and B is $CR_4R_5$; R, $R_2$, $R_3$, $R_4$, $R_5$ and $R_6$ are each a hydrogen, and $R_1$ is $C(=O)(CH_2)_n NR'R''$ and $(CH_2)_n CHOHCH_2 NR'R''$, n being 0–5.

Preferably, this method of treatment with the compositions of the present invention is used as an adjunct or additive therapy for patients with implanted defibrillators, in order to combine the electrical defibrillation with the chemical defibrillation. The utility of such a combination has been previously shown [M. T. Neuman, PhD Thesis, 1995, Tel Aviv University, Tel Aviv, Israel].

Herein, the term "treating" includes substantially inhibiting or completely stopping episodes of cardiac dysfunction, such as ventricular fibrillation, in a subject.

Herein, the term "preventing" refers to a method for barring a subject from exhibiting symptoms of a cardiac disorder, such as ventricular fibrillation, or alternatively for at least reducing the likelihood and/or severity of such symptoms arising in the subject. Further according to the present invention there is provided a method of locally treating a disorder of a tissue of a subject comprising the step of locally applying the herein above described composition to the tissue. The method includes the steps of applying the composition to an implant and inserting the implant into a tissue, such as cardiac tissue, Alternatively, the composition can be applied to a transdermal patch, which is applied to the skin for system absorption.

Also according to the present invention, there is provided a method for preventing ischemia in the cardiac tissue of a subject, by administering the above-referenced compound of the present invention to the subject.

A precise understanding of the mechanism by which the tricyclic compounds of the present invention cause such chemical defibrillation is not required in order to practice the present invention. However, while not wishing to be bound to any particular mechanism or theory, it is believed that increased catecholamine levels, induced by the compounds of the present invention, are involved in the process. Several lines of evidence support this hypothesis. For example, the evaluation of intra- and inter-species differences for the ability to defibrillate spontaneously have indicated the central role of cardiac autoregulation. In particular, TVF appears in animals with predominantly sympathetic autoregulation, while SVF appears in animals with predominantly vagal autoregulation. Within members of the same species, the ability to defibrillate spontaneously is a normal feature of young mammals, and this ability decreases with age. Respectively, cardiac autoregulation in young mammals is dominantly sympathetic and turns to a vagal predominance with age.

Furthermore, administration of either β-adrenergic blockers (e.g., propranolol or pindolol) or a parasympathomimetic agonist (e.g., acetylcholine or metacholine) in mammals exhibiting TVF, prolongs the duration of TVF and even transforms it into SVF. Lastly, self-defibrillation requires a relatively high degree of intercellular synchronization, which may be enhanced by elevated catecholamine levels. Thus, compounds which are known to elevate extraneuronal catecholamine levels in the heart, such as dibenzoazepins and phenothiazines, were identified to enhance ventricular self-defibrillation, an effect abolished by co-administration of β-adrenergic blockers [9, 14].

Furthermore, in a recent publication, the efficacy in defibrillating activity of dibenzoazepins and phenothiazines was directly related to their ability to inhibit noradrenaline uptake [10]. Alternatively, the compound, 11-Oxo-10,11-dihydro-5-(N-methyl)-propylaminodibenzo[b,e] [1,4] diazepin, was previously suggested for application as a muscarinic receptor antagonist in PCT Application No. WO 91/10654), supporting the role of sympathetic predominance in potential defibrillating activity.

Thus, further according to the present invention there is provided a method of treating or preventing a cardiac disorder in a subject, by inducing cardiac sympathetic activity by administering the tricyclic compounds of the present invention as hereinabove described.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion. The following protocols and experimental details are referenced in the Examples that follow.

Example 1

Synthesis of 10,11-dihydro-5-[(3-N-alkyl)1-oxopropyl] 5-H-dibenzo[b,f]azepin Monohydrochloride Compounds Synthesis of 10.11-dihydro-5-[(3-chloro)1-oxopropyl]-5H-dibenzo[b,f]azepin: The synthesis was performed as known in the literature (Schindler W.; Hafliger F.; *Helvetica Chima Acta* 1954, 59, 472–483). To a solution of 5H-10,11-dihydro-dibenzo[b,t]azepin (0.85 gr., 4.359 mmol) in benzene (50 ml), 0.5 ml 3-chloropropionyl chloride (5.225 mmol) was added dropwise. The mixture was refluxed for 3 h, the solvent was removed under reduced pressure and the residue was washed with 5% aq. HCl, followed by extraction with CH$_2$Cl$_2$ (20 ml). The resulting organic layer was dried over Na$_2$SO$_4$, and the crude product was purified by flash chromatography (silica gel, hexane-ethyl acetate 8:2), resulting in 1.133 gr. (91% yield) of 10,11-dihydro-5-[(3-chloro)1-oxopropyl]-5-H-dibenzo[b,f]azepin, in the form of white crystals. NMR (CDCl$_3$): 7.16 (bs, 8H), 3.82 (m, 2H), 3.46 (m, 1H), 2.85 (m, 2H), 2.51(m, 1H). MS (CI): 286 (M$^+$).

Scheme 1 below illustrates the synthesis and structure of 10,11 dihydro-5-[(3-chloro)1-oxopropyl]-5-H-dibenzo[b,f]azepin:

SCHEME 1 (10)

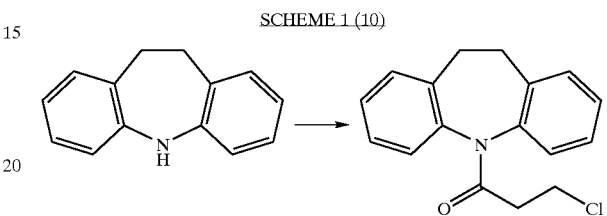

Synthesis of 10,11-dihydro-5-[(3-N alkyl)1-oxopropyl]5-H-dibenzo[b,f]azepin monohydrochloride: Synthesis of 10,11-dihydro-5-[(3-N-alkyl)1-oxopropyl]5-H-dibenzo[b,f] azepin derivatives was achieved by reaction of the 10,11-dihydro-5-[(3-chloro)1-oxopropyl]5-H-dibenzo[b,f]azepin as a starting material with the corresponding alkyl amine. The succeeding derivatives, wherein the 3-N-substituted alkyl is a methyl, an ethyl or an iso-propyl, (compounds 15a–c) were prepared following the below-described general procedure. A well-stirred suspension of 10,11-dihydro-5-[(3-chloro)-1-oxopropyl]-5-H-dibenzo [b,f]azepin (1.71 gr., 6.0 mmol) in ethanol (50 ml) was warmed to 65° C. Alkylamine (10 mmol) was added dropwise. The mixture was stirred for 1 h at 65° C., and then allowed to cool to room temperature. The mixture was washed with 5% aq. potassium bicarbonate and extracted with CH$_2$Cl$_2$ (20 ml). The organic layer was dried over Na$_2$SO$_4$, filtered and the solvent was removed under reduced pressure. The crude product was recrystallized from EtOAc at 0° C. The precipitate was filtered to result in the appropriate free base. The solid was then dissolved in toluene and HCl was bubbled till a precipitate formed. The precipitate was filtered and dried under reduced pressure resulting in the appropriate monohydrochloride salt. Alternatively, wherein bulkier alkyl groups were used for substituting the 3-N alkyl, such as tert-butyl, sec-butyl, iso-butyl and benzyl (compounds 15d–g), the following procedure was used: A solution of 10,11-dihydro-5-[(3-chloro)1-oxopropyl]-5-H-dibenzo[b,f] azepin (0.285 gr., 1.0 mmol) in iso-propanol (15 ml) and monoamine (15 ml) was refluxed overnight. The solvent was removed under reduced pressure, and the crude product was recrystallized from EtOAc at 0° C. The solid was dissolved in toluene and HCl was bubbled till a precipitate was formed. The precipitate was filtered and dried under reduced pressure resulting in the appropriate monohydrochloride salt.

Scheme 2 below illustrates the synthesis and general structure of 10,11-dihydro-5-[(3-N-alkyl)1-oxopropyl]-5-H-dibenzo[b,f]azepin monohydrochloride of both synthetic routes:

SCHEME 2 (15)

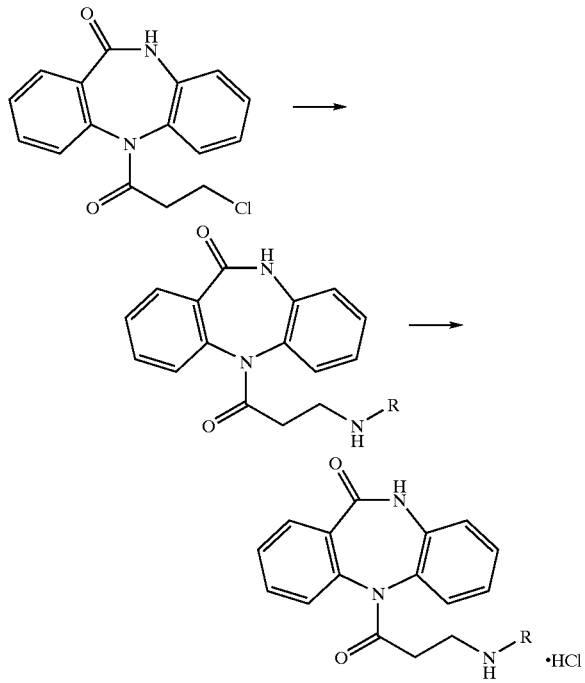

(i) 10.11-dihydro-5-[(3-N-methyl)-1-oxopropyl-5-H-dibenzo [b,f]azepin monohydrochloride: The synthesis was performed according to the above synthetic scheme. 1.126 gr. (67% yield) of light yellow solid was obtained. $^1$H NMR (D$_2$O): δ 6.87 (brm, 8H), 3.15 (s, 1H), 2.82 (brm, 4H), 2.47 (s, 3H), 2.24 (brm, 3H). FAB/MS 281(M$^+$).

Scheme 3 below illustrates the structure of 10,11-dihydro-5-[(3-N-methyl)1-oxopropyl]5-H-dibenzo[b,f]azepin monohydrochloride:

SCHEME 3 (15 a)

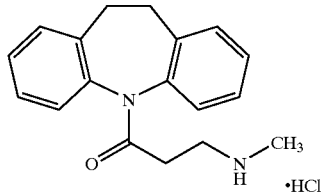

(ii) 10,11-dihydro-5-[(3-N ethyl)1-oxopropyl] 5-H-dibenzo[b,f]azepin monohydrochloride: The synthesis was performed according to the above synthetic scheme. 1.129 gr. (64% yield) of light yellow solid was obtained. $^1$H NMR (D$_2$O): δ 6.89 (brm, 8H), 3.12 (s, 1H), 2.84 (brm, 7H), 2.27 (brm, 2H), 1.02 (t, J=7.4, 3H). FAB/MS 295 (M$^+$).

Scheme 4 below illustrates the structure of 10,11-dihydro-5-[(3-N-ethyl)1-oxopropyl]5-H-dibenzo[b,f]azepin monohydrochloride:

SCHEME 4 (15 b)

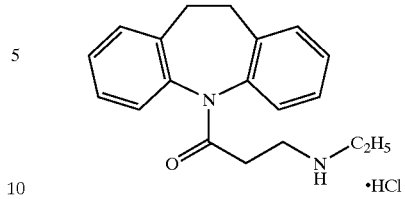

(iii) 10.11-dihydro-5-l(3-N-iso-propyl)1-oxopnropyl]5-H-dibenzo [b,f]azepin monohydrochloride, The synthesis was performed according to the above synthetic scheme. 1.219 gr. (66% yield) of light yellow solid was obtained, with mp 199.1° C. $^1$H NMR (D$_2$O): δ 6.97 (brm, 8H), 3.14 (m, 1H), 2.97 (m, 4H), 2.67 (m, 1H), 2.42 (m, 1H), 2.38 (m, 2H), 1.08 (d, J=6.6, 6H). FAB/MS 309 (M$^+$).

Scheme 5 below illustrates the structure of 10,11-dihydro-5-[(3-N-iso-propyl)1-oxopropyl] 5-H-dibenzo[b,f]azepin monohydrochloride:

SCHEME 5 (15 c)

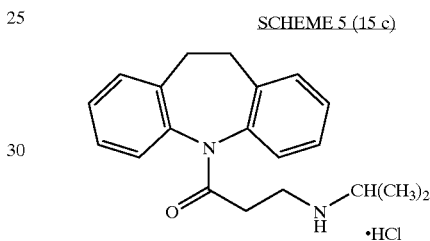

(iv) 10.11-dihydro-5-[(3-N-tert butyl)1-axoprogyl]5-H-dibenzo [b,f]azepin monohydrochloride: The synthesis was performed according to the above synthetic scheme. 280 mgr. (87% yield) was obtained. $^1$H NMR (CDCL$_3$): δ 7.24 (m, 8H), 3.39 (m, 2H), 2.85 (m, 5H), 2.51 (m, 1H), 1.26 (m, 9H). FAB/MS 323 (M$^+$).

Scheme 6 below illustrates the structure of 10,11-dihydro-5-[(3-N-tert-butyl)1-oxopropyl] 5-H-dibenzo[b,f]azepin monohydrochloride:

SCHEME 6 (15 d)

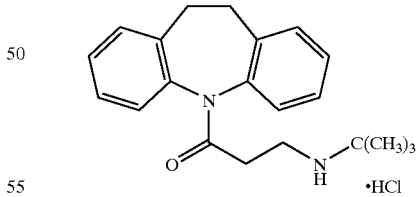

(v) 10,11-dihydro-5-[(3-N-sect-butyl)1-oxopronyl]5-H-dibenzo [b,f]azepin monohydrochloride, The synthesis was performed according to the above synthetic scheme. 241 mg. (75% yield) was obtained. $^1$H NMR (CDCl$_3$): δ 7.25 (m, 8H), 3.37 (m, 2H), 2.97 (m, 5H), 2.79 (m, 2H), 1.52 (m, 2H). 0.99 (m, 6H). FAB/MS 323 (M$^+$).

Scheme 7 below illustrates the structure of 10,11-dihydro-5-[(3-N-sect-butyl)1-oxopropyl] 5-H-dibenzo[b,f]azepin monohydrochloride:

SCHEME 7 (15 e)

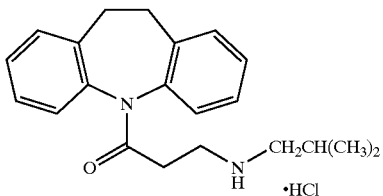

(vi) 10,11-dihydro-5-[(3-N-iso-butyl)1-oxopropyl]5-H-dibenzo [b,f]azepin monohydrochloride: The synthesis was performed according to the above synthetic scheme. 264 mg. (82% yield) was obtained. $^1$H NMR (CDCl$_3$): δ 7.23 (m, 8H), 3.35 (m, 2H), 2.82 (m, 4H), 2.47 (m, 2H), 1.84 (m, 1H), 0.95 (d, J=6.6 Hz, 3H), 0.89 (d, J=6.6 Hz, 3H). FAB/MS 323 (M$^+$).

Scheme 8 below illustrates the structure of 10,11-dihydro-5-[(3-N-iso-butyl)1-oxopropyl] 5-H-dibenzo[b,f]azepine monohydrochloride:

SCHEME 8 (15 f)

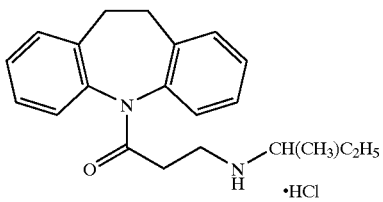

(vii) 10,11-dihydro-5-[(3-N-benzyl)1-oxopropyl]5-H-dibenzo [b,f]azepin monohydrochloride: The synthesis was performed according to the above synthetic scheme. 367 mg. (67% yield) was obtained. $^1$H NMR (CDCl$_3$): δ 7.23 (m, 8H), 3.35 (m, 2H), 2.82 (m, 4H), 2.47 (m, 2H), 1.84 (m, 1H), 0.95 (d,J=6.6 Hz., 3H), 0.89 (d, J=6.6 Hz, 3H). FAB/MS 357 (M$^+$).

Scheme 9 below illustrates the structure of 10,11-dihydro-5-[(3-N-benzyl)1-oxopropyl] 5-H-dibenzo[b,f]azepine monohydrochloride:

SCHEME 9 (15 g)

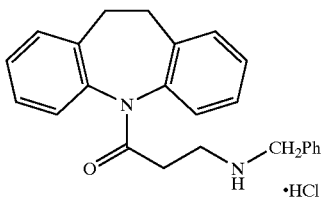

Scheme 9a describes the synthesis of the β-amino alcohol derivative according to the present invention, which was performed in two stages.

SCHEME 9a

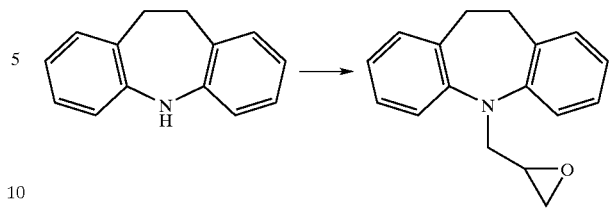

10,11-dihydro-5-[N-2 methyloxirane]5-H-dibenzo[b,f]azepin (20), 20r, 20s (stage 1):

To a solution of 5H-10,11-dihydro-dibenzo[b,f]azepin (1.320 g, 6.711 mmol, see Scheme 1, above) in benzene (50 ml) was added NaNH$_2$ (0.5 gr). The mixture was refluxed for 2 hr and epichlorohydrin (1 ml, 12.810 mmol) was added dropwise. The mixture was refluxed for 6 hr. The solvent was removed under reduced pressure, and the residue was washed with 5% aq HCl, and extracted with CH$_2$Cl$_2$ (20 ml). The organic layer was dried over Na$_2$SO$_4$ and the crude product was purified by flash chromatography (silica gel, hexane-ethyl acetate 9.5:0.5) to give 20, (0.75 g, 45%) in the form of white powder. $^1$H NMR (chloroform): 7.07 (bs, 4H), 6.93 (m, 2H), 6.73 (bt, 2H) 3.91 (m, 2H), 3.16 (m, 4H), 3.05 (m, 1H), 2.67 (d, 1H), 2.55 (d, 1H). MS (CI): 251 (M$^+$). (scheme 9b)

SCHEME 9b

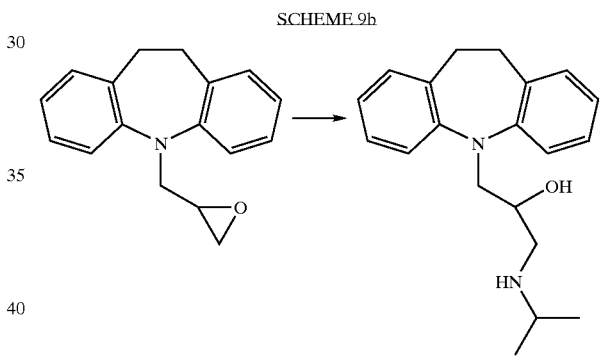

10,11-dihydro-5-[N-β iso-propylamino-2propanol]5-H-dibenzo[b,f]azepin monohydrochloride, 25 bi, 25 bis, 25 bir (stage II)

General procedure: A suspension of 20 (1.5 g, 5.0 mmol) in iso-propanol (50 ml) was warmed to 30° C., iso-propyl amine (10 mmol) was added dropwise, the mixture was stirred overnight at this temperature and then allowed to cool to room temperature. The solvent was removed under reduced pressure, and the crude product was recrystallized from ethyl acetate at 0° C. The precipitation was filtered to give the appropriate free base. The solid was dissolved in toluene and HCl was bubbled until a precipitate reappeared. The precipitation was filtered and dried under reduced pressure to give 25 bi salt. $^1$H NMR (chloroform): 7.07 (bs, 4H), 6.93 (m, 2H), 6.73 (bt, 2H) 3.79 (m, 1H), 3.15 (s, 4H), 2.78 (m, 1H), 2.72 (d, 2H), 2.55 (d, 2H), 1.01 (d, 6H). MS (CI): 311(M$^+$).

Example 2

Synthesis of 11-Oxo-10,11-dihydro-5-[(N-alkyl)oxopropyl]-5-H-dibenzo[b,e][1.4]diazepin Monohydrochloride Compounds Synthesis of 11-Oxo-10, 11-dihydro-5H-dibenzo [be][1,4] diazepin: The synthesis was performed according to the below synthetic scheme. A suspension of 2-chlorobenzoic acid (5.08 gr., 31.81 mmol), o-phenylenediamine (3.46 gr., 31.48 mmol), copper powder (2.14 gr., 31.7 mmol) and molecular sieves (3A) in chlorobenzene (100 ml) was vigorously stirred at 130° C. for 8 h. The hot mixture was rapidly filtered and the filtrate was concentrated under reduced pressure. The solid precipitate was collected by filtration and then recrystallized from EtOH resulting in 11-Oxo-10,11-dihydro-5H-dibenzo[b,e][1,4] diazepin 5.48 gr. (82% yield) in the form of bright yellow powder. $^1$H NMR (acetone): 8.89 (s, 1H), 7.80 (d, J=7.7 Hz., 1H), 7.33 (t, J=7.3 Hz., 1H), 7.07 (m, 6H). FAB/MS: 211 (M$^+$).

Scheme 10 below illustrates the synthesis and structure of 11-Oxo-10,11-dihydro-5H-dibenzo[b,e][1,4] diazepin monohydrochloride:

SCHEME 10 (1)

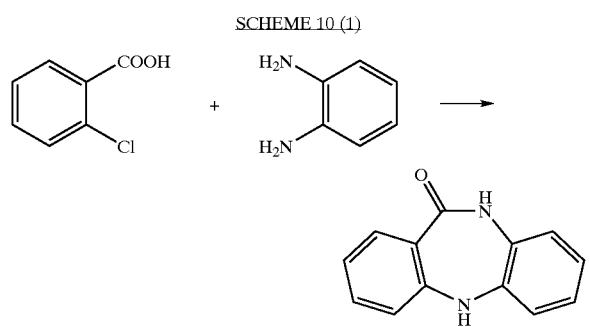

Synthesis of 11-Oxo-10.11-dihydro-5-[(3-chloro)1-oxopropyl] 5-H-dibenzo[b,e] [1,4]diazepin: The synthesis was performed according to the below synthetic scheme. To a solution of 11-Oxo-10,11-dihydro-5H-dibenzo[b,e][1,4] diazepin (0.376 gr., 1.79 mmol) in dry THF, (10 ml) NaNH$_2$ (0.132 gr., 3.39 mmol) was added. The mixture was cooled to 0° C., and 0.2 ml 3-chloropropionyl chloride (2.09 mmol) was added dropwise. The mixture was stirred for 30 min at 0° C., allowed warming to room temperature, washed with 5% aq. potassium bicarbonate and extracted with CH$_2$Cl$_2$ (20 ml). The resulting organic layer was dried over Na$_2$SO$_4$, filtered and the solvent was removed under reduced pressure. The crude product was crystallized from ether, resulting in 0.467 gr. (87% yield) of 11-Oxo-10,11-dihydro-5-[(3-chloro)1-oxopropyl] 5-H-dibenzo[b,e] [1,4] diazepin in the form of a yellow solid, mp 241–242° C. $^1$H NMR (CDCl$_3$): 8.78 (s, 1H), 7.98 (s, 1H), 7.59 (s, 1H), 7.4–7.26 (m, 6H), 3.77 (m, 4H). FAB/MS: 301(M$^+$).

Scheme 11 below illustrates the synthesis and structure of 11-Oxo 10,11-dihydro-5-[(3-chloro)1-oxopropyl] 5-H-dibenzo[b,e][1,4] diazepin:

SCHEME 11 (6)

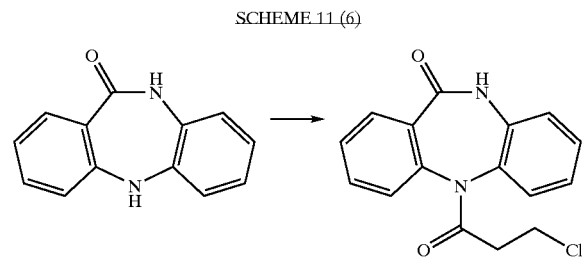

Synthesis of 11-Oxo-10,11-dihydro-5 [(N-alkyl)1-oxopropyl]5-H-dibenzo[b,e,][1,4]diazepin monohydrochloride: The synthesis of the below described 11-Oxo-10,11-dihydro-5-[(N-alkyl)1-oxopropyl]5-H-dibenzo [b,e][1,4] diazepin hydrochloride compounds, 11a–c, was performed by reacting 11-Oxo-10,11-dihydro-5-[(3-chloro)1-oxopropyl]-5-H-dibenzo[b,e][1,4]diazepin, as a starting material, with the appropriate alkyl amine. A well-stirred suspension of 11-Oxo-10,11-dihydro-5-[(3-chloro)1-oxopropyl]-5-H-dibenzo[b,e][1,4] diazepin (1.5 gr., 5.0 mmol) in ethanol (50 ml) was warmed to 65° C. Alkylamine (10 mmol) was added dropwise. The mixture was stirred for 1 h at 65° C., and then allowed to cool to room temperature. The mixture was then washed with 5% aq. Potassium bicarbonate and extracted thrice with CH$_2$Cl$_2$ (20 ml). The organic layer was dried over Na$_2$S$_4$, filtered and the solvent was removed under reduced pressure. The crude product was recrystallized from EtOAc at 0° C. The precipitate was filtered to result in the appropriate free base. The solid was then dissolved in toluene and HCl was bubbled till a precipitate formed. The precipitate was filtered and dried under reduced pressure resulting in the appropriate hydrochloride salt.

Scheme 12 below illustrates the synthesis and general structure of 11-Oxo-10,11-dihydro-5-[(N-alkyl)1-oxopropyl]5-H-dibenzo[b,e] [1,4]diazepin monohydrochloride:

SCHEME 12 (11)

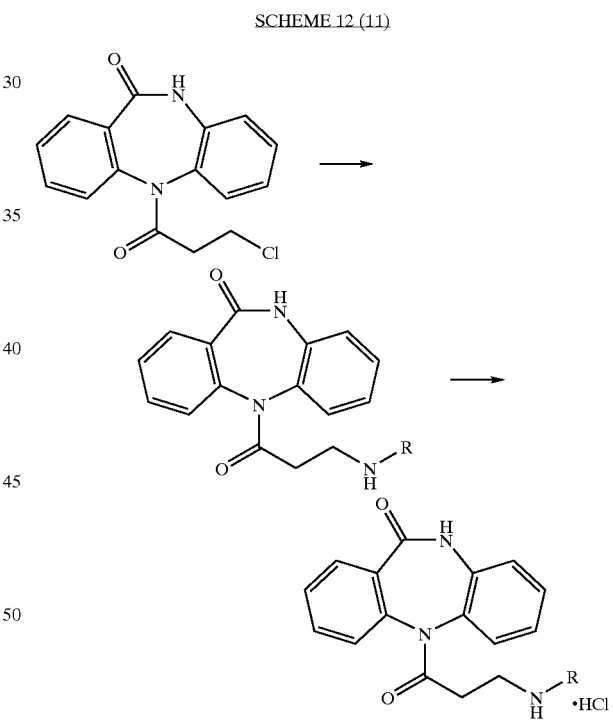

(i) Synthesis of 11-Oxo-10,11-dihydro-5-[(N-methyl)1-oxopropyl] 5H dibenzo[b,e] [1,4] diazepin monohydrochloride: The synthesis was performed according to the above synthetic scheme. The compound, in the form of a light-pink solid was obtained, 627 mg. (44% yield), with mp=223–225° C. $^1$H NMR (D$_2$O): δ 7.33 (br m, 8H), 3.06 (t, J=6 Hz, 2H), 2.9 (m, 1H), 2.48 (s, 3H), 2.36 (br m, 1H). FAB/MS 297 (M').

Scheme 13 below illustrates the structure of 11-Oxo-10, 11-dihydro-5-[(3-N-methyl)1-oxopropyl] 5-H-dibenzo[b,e] [1,4] diazepin monohydrochloride:

SCHEME 13 (11 a)

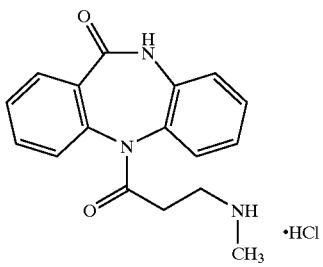

(ii) Synthesis of 11-Oxo-10,11-dihydro-5-[(N-ethyl)1-oxopropyl]5-H-dibenzo [b,e][1,4]diazepin monohydrochloride: The synthesis was performed according to the above synthetic scheme. The compound, in the form of light-yellow solid, was obtained, 1.023 gr. (66% yield), with mp 243–245° C. $^1$H NMR (D$_2$O): 7.40 (br m, 8H), 3.08 (t, J=6.1 Hz, 2H), 2.86 (m, 3H), 2.38 (m 1H), 1.06 (t, J=7.3, 3H). FAB/MS: 311 (m$^+$). Scheme 14 below illustrates the structure of 11-Oxo-10,11-dihydro-5-[(N-ethyl)1-oxopropyl]-5-H-dibenzo [b,e][1,4] diazepin hydrochloride:

SCHEME 14 (11 b)

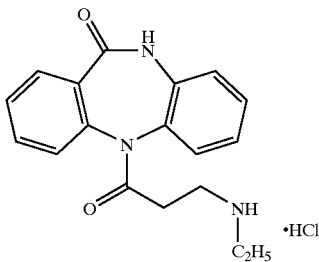

(iii) Synthesis of 11-Oxo-10,11-dihydro-5-[(N-iso-propyl)-1-oxopropyl]-5-H -dibenzo[b,e][1,4] diazepin monohydrochloride: The synthesis was performed according to the above synthetic scheme. The compound, in the form of light-orange solid, was obtained, 791 mgr. (49% yield). $^1$H NMR (D$_2$O): 7.35 (br m, 8H), 3.05 (br m, 3H), 2.85 (m, 1H), 2.33 (m, 1H), 1.08 (t, J=7.3, 3H). FAB/MS: 323 (m$^+$).

Scheme 14 below illustrates the structure of 11-Oxo-10, 11-dihydro-5-[(N-iso-propyl)1-oxopropyl] 5-H-dibenzo [b,c] [1,4] diazepin monohydrochloride:

SCHEME 15 (11 c)

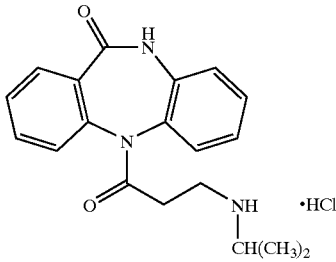

Example 3
Synthesis of 10,11-dihydro-5-[N-β isopropylamino-2propanol] 5-H-dibenzo [b,f]azepin (25bi). 25bir, 25bis Monohydrochloride Compounds 10,11-dihydro-5-[N-2 Methyloxirane]5-H-dibenzo[b,f] azepin (20). 20r, 20s:, To a solution of 5 (1.320 g, 6.711 mmol) in benzene (50 mL) was added NaNH$_2$ (0.5 gr). The mixture was refluxed for 2 hr and the appropriate epichlorohydrin (1 mL, 12.810 mmol) was added dropwise (racemic to obtain 20, R enantiomer to obtain 20r and S enantiomer to obtain 20s. The mixture was refluxed for 6 hrs. The solvent was removed under reduced pressure, and the residue was washed with 5% aq HCl, and extracted with CH$_2$Cl$_2$ (2×20 mL). The organic layer was dried over Na$_2$SO4 and the crude product was purified by flash chromatography (silica gel, hexane-ethyl acetate 9.5:0.5) to give 20, (0.75 g, 45%) in the form of white powder. 1H NMR (chloroform): 7.07 (bs, 4H), 6.93 (m, 2H), 6.73 (bt, 2H) 3.91 (m, 2H), 3.16 (m, 4H), 3.05 (m, 1H), 2.67 (d, 1H), 2.55 (d, 1H). MS (CI): 251 (M+).

Scheme 16 below illustrates the synthesis and structure of 10,11-dihydro-5-[N-2 methyloxirane]5-H-dibenzo[b,f] azepin (20), 20r. 20s

SCHEME 16 (20, 20r, 20s)

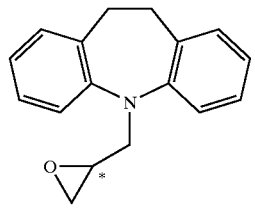

10,11-dihydro-5-[N-β isopropylamino-2propanol)] 5-H-dibenzo [b,f]azepin monohydrochloride, 25 bi, 25 bis, 25 bir:

General procedure: A suspension of 20 (1.5 g, 5.0 mmol) in iso-propanol (50 ml) was warmed to 30° C., iso-propylamine (10 mmol) was added dropwise, the mixture was stirred overnight at this temperature and then allowed to cool to room temperature. The solvent was removed under reduced pressure, and the crude product was recrystallized from ethyl acetate at 0° C.

The precipitation was filtered to give the appropriate free base. The solid was dissolved in toluene and HCl was bubbled until) a precipitation reappeard. The precipitation was filtered and dried under reduced pressure to give 25 bi salt. 1H NMR (chloroform): 7.07 (bs, 4H), 6.93 (m, 2H), 6.73 (bt, 2H) 3.79 (m, 1H), 3.15 (s, 4H), 2.78 (m, 1H), 2.72 (d, 2H), 2.55 (d, 2H), 1.01 (d, 6H). MS (CI): 311 (M+).

Scheme 17 below illustrates the synthesis and structure of 10,11-dihydro-5-[N-β isopropylamino-2propanol)]5-H-dibenzo[b,f]azepin monohydrochloride, 25 bi, 25 bis and 25 bir.

SCHEME 17 (25bi, 25bir, 25bis)

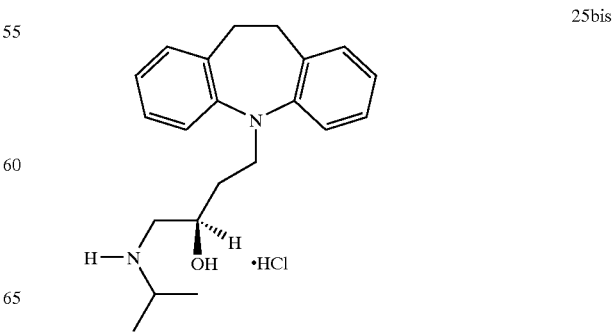

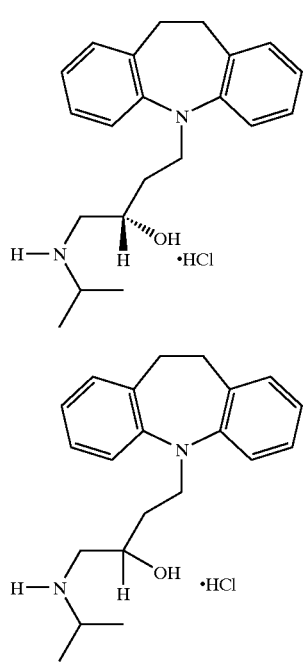

25bir

25bi

Example 4

Antiarrhythmic Defibrillating Activity of Tricyclic Dibenzoazepin and 11-Oxo-dibenzodiazepin Compounds 10,11-dihydro-5-[(3-N-alkyl)1-oxopropyl] 5-H-dibenzo [b,f]azepin monohydrochloride, 10,11-dihydro-5-[N-? isopropylamino-2propanol)] 5-H-dibenzo [b,f]azepin monohydrochloride and 11-Oxo-10,11-dihydro-5-[(N-alkyl)1-oxopropyl]-5-H-dibenzo [b,e] [1,4] diazepin hydrochloride were synthesized as is described hereinabove and tested for their effectiveness in transforming SVF to TVF, as described herein. The desired outcome was determined to be the ability of the drug molecule to reduce or abolish the occurrence of artificially induced SVF, and its transformation to the spontaneously defibrillating TVF. The experimental method was as follows.

Hydrochloride salts of the compounds were dissolved in saline. Activity of each compound was tested in cats of both sexes. Cats were anesthetized with 15–25 mg/kg intravenous sodium, pentobarbital. The tested compounds were injected intravenously (1–3 mg/kg). The heart of each experimental subject was exposed through midline thoracotomy, and a room air respirator was applied through a tracheal cannula. Lead II electrocardiogram and intra-arterial blood pressure was recorded on a Grass Polygraph (Grass Instrument Co., Quincy, Mass., USA).

Fibrillating stimuli (a train of rectangular pulses of 2 to 15 V, 100 pulses/sec and duration of 0.1 to 1.0 msec, for a period of 1 sec) were delivered through two silver needle electrodes attached to the pericardium on the left ventricle. Fibrillating stimuli were one and a half to twice the strength of the fibrillating threshold.

Animals were designated as having SVF if VF failed to terminate spontaneously within 90 see, and required electrical defibrillation. Animals that exhibited two to five consecutive episodes of VF of short (20 to 60 sec) duration were designated as having TVF. VF was induced before and after drug administration, according to a previously described procedure [13]. The type of VF was examined before and 2 to 3 min after drug treatment. Each cat served as its own control. In some experiments, a β-adrenergic blocker (propranolol, 0.1–0.6 mg/kg) was administered after drug administration, in order to evaluate the neutralizing effect of the blocker on the compound-induced catecholamine levels. Table 1 below presents the results.

TABLE 1

| Compound | Relative activity in dosage of 1 mg/kg | Relative activity in dosage of 2 mg/kg | Relative activity in dosage of 3 mg/kg |
|---|---|---|---|
| 15a | 50% | 67% | 100% |
| 15b | 50% | 75% | 100% |
| 15c | 64% | 67% | 83% |
| 15d | 44% | 67% | 100% |
| 15e | 0 | 0 | 33% |
| 15f | 0 | 0 | 0 |
| 15g | 0 | 0 | 0 |
| 11a | 0 | — | 50% |
| 11b | 0 | 50% | 50% |
| 11c | 0 | 0 | 0 |
| 25bi | 100% | 100% | — |
| 25bir | 50% | 100% | — |
| 25bis | 100% | 100% | — |

Example 5

Suitable Formulations for Administration of Tricyclic Dibenzoazepin and 11-Oxo-dibenzodiazepin Compounds The tricyclic dibenzoazepin and 11-Oxo-dibenzodiazepin derivatives of the present invention, including free base or salt form, can be administered to a subject in a number of ways, which are well known in the art. Hereinafter the term "tricyclic dibenzoazepin derivatives" refers to the group of dibenzoazepin derivatives in free base form and the group of dibenzoazepin derivatives in a salt form. Hereinafter the term "tricyclic dibenzodiazepin derivatives" refers to the group of dibenzodiazepin derivatives in free base form and the group of dibenzodiazepin derivatives in a salt form. Hereinafter, the term "subject" refers to the human or any lower animal to which the tricyclic dibenzoazepin or 11-Oxo-dibenzodiazepin derivative is administered. For example, administration may be done topically (including ophthalmically, vaginally, rectally, intranasally), orally, or parenterally, for example by intravenous bolus or drip, intraperitoneal, subcutaneous, or intramuscular (cardiac) injection.

Formulations for topical administration may include but are not limited to lotions, ointments, gels, creams, suppositories, drops, liquids, sprays, transdermal patches and powders. Conventional pharmaceutical carriers, aqueous, powder or oily bases, thickeners and the like may be necessary or desirable. In addition to the formulations described previously, a compound of the present invention may also be formulated as a depot preparation. Such long acting formulations may be administered by implantation (for example subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives such as sparingly soluble salts.

Compositions for oral administration include powders or granules, suspensions or solutions in water or non-aqueous media, sachets, capsules of tablets. Thickeners, diluents, flavorings, dispersing aids, emulsifiers or binders may be desirable.

Formulations for parenteral administration may include but are not limited to sterile aqueous solutions, which may also contain buffers, diluents and other suitable additives.

Dosing is dependent on the severity of the symptoms of arrhythmic or fibrillating occurrence ad an the responsiveness of the subject to the tricyclic dibenzoazepin derivatives. Persons of ordinary skill in the art can easily determine dosages, dosing methodologies ad repetition rates.

Example 6

Method of Treatment or Prevention of Ventricular Fibrillation

As noted above, the compounds of the present Invention, which are tricyclic dibenzoazepin and 11-Oxo-dibenzodiazepin derivatives, have been shown to be effective defibrillating agents. To following example is an illustration only of a method of treating VF with the dibenzoazepin and 11-Oxo-dibenzodiazepin derivatives, and is not intended to be limiting.

The method includes the step of administering the tricyclic dibenzoazepin or 11-Oxo-dibenzodiazepin derivatives, in a pharmaceutically acceptable carrier as described in Example 5 above, to a subject to be treated. The tricyclic dibenzoazepin or 11-Oxo-dibenzodiazepin derivative is Administered according to an effective dosing methodology, preferably until a predefined endpoint is reached, such as the prevention of VP occurrence or abnormal cardiac activity. Optionally and preferably the compound is administered parenterally.

According to another preferred embodiment of the present invention, the compound is used as an adjunct or additive treatment for a patient who has received an implanted defibrillator, such that the compound is administered to the patient as previously described.

Example 7

Method of Manufacture of a Medicarnent Containing a Tricyclic Dibenzoazepin and 11-Oxo-dibenzodiazepin Derivative The following is an example of a method of manufacturing a tricyclic dibenzoazepin and 11-Oxo-dibenzodiazepin derivative. First, the tricyclic dibenzoazepin or 11-Oxo-dibenzodiazepin derivative is synthesized in accordance with good pharmaceutical manufacturing practice. Examples of methods of synthesizing the tricyclic dibenzoazepin and 11-Oxo-dibenzodiazepin derivatives were given previously herein. Next, the tricyclic dibenzoazepin or 11-Oxo-dibenzodiazepin derivative is placed in a suitable pharmaceutical carrier, as described is Example 3 above, again in accordance with good pharmaceutical manufacturing practice.

It will be appreciated that the above descriptions are intended only to serve as examples, and that many other embodiments are possible within the spirit and the scope of the present invention.

Although to invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF REFERENCES CITED

1. Olshausen K. V., Win T., Pop T., Treese N., Bethge K, Meyer J. Sudden cardiac death while wearing a Holter monitor. Am. J. Cardiol., 67: 381–386, 1991.
2. Vaughan Williams E. M. Classification of antiarrhythmic drugs. In: Sandoe E., Flasted-Jansen E, Oldsen K. H., eds, Symposium on Cardiac Arrythmias, Sudertalje Sedan: A B Astra, pp, 449–472,1970.
3. Sanna G., Archidiacomo R. Chemical ventricular difibrillation of the human heart with bretylium tosylate. Am. J. Cardiol. 32:982–486, 1973.
4. CAST Investigators. Preliminary report: Effect of ecainide and flecainide on mortality in a randomized trial of arrhythmia suppression after myocardial infarction N. Engl. J. Med. 321: 406–412, 1989.
5. CAST II Investigators—Effect of the antiarrhythmic agent on after myocardial infarction, N. Engl. J. Med. 327:227–233, 1992.
6. Manoach M., Varon D., Neuman M., Erez M. Editorial—A new group of defibrillatory drugs in the classification of antiarrhythmic agents. Int. J. Cardiol. 21:211–217, 1988.
7. Manoach M., Varon D, Erez M. The role of catecholamines on intercellular coupling, myocardial cell synchronization and self ventricular defibrillation. Mol. Cell. Biochem. 147:181–185, 1995.
8. Manoach M., Erez M., Varon D, Properties required for self ventricular defibrillation: Influence of age and drugs. Cardiol. Elderly. 1: 337–344, 1993.
9. Manoach M., Beker B., Erez M., Varon D, Netz H. Spontaneous termination of electrically induced ventricular fibrillation. In: MacFarlane P. W. ed. Progress in Electrophysiology, London: Pitman Medical Publications Ltd, pp. 361–365,1979.
10. Erez M., Varon D. Dibenzazepines and phenothiazines—A winding path to defibrillatory antiarrhythmic agents. Exp. Clin. Cardiol. 2; 59–63,1997.
11. Kaverina N. V., Sloldinov A. P. New cardiovascular drugs among

What is claimed is:

1. A compound having a general formula (II):

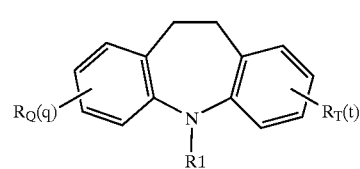

[II]

wherein $R_1$ is a cycloalkyl with $R_Q$ and $R_T$ each independently selected from the group consisting of a hydrogen, a hydroxyl, a saturated, unsaturated, aliphatic, or branched, alkyl, a substituted or unsubstituted $(CH_2)_m$-(hetero)aryl, a sulfonylamide, and a pharmaceutically acceptable salt thereof; q and t are each an integer independently selected from 1–4; or wherein $R_1$ is an amino-alcohol being $(CH_2)_n CHOHCH_2NR'R''$ with q and t each an integer independently selected from 1–4, wherein for n being 0 or I, R', $R_Q$, $R_T$, are each a hydrogen and R" is selected from the group consisting of a branched alkyl, a substituted or unsubstituted $(CH_2)_n$-(hetero)aryl, m being 0–5 a sulfonylamide, and a pharmaceutically acceptable salt thereof, and wherein for n being 2–5, R', $R_Q$, $R_T$, are each a hydrogen and R" is selected from the group consisting of a hydrogen, a halogen, a hydroxyl, a saturated, unsaturated, aliphatic, or branched, alkyl, a substituted or unsubstituted $(CH_2)_m$-(hetero)aryl, a sulfonylamide, and a pharmaceutically acceptable salt thereof.

2. The compound of claim 1, wherein n is 2 and R" is an alkyl selected from the group consisting of propyl, n-butyl, tert-butyl and with the proviso that R" is not a methyl or an ethyl moiety.

3. The compound of claim 1, wherein n is 1 or 2 and R" is saturated or unsaturated $(CH_2)_m$-cycloalkyl or $(CH_2)_m$-(hetero)aryl, m being 0–5.

4. The compound of claim 3, wherein m is 1 and R" is an aromatic 6-member ring.

5. The compound of claim 1, wherein said R1 is in a form selected from the group consisting of an R enantiomeric form, an S enantiomeric form, and a racemic mixture thereof.

6. A composition for treating cardiac arrhythmia, comprising a pharmaceutically affective amount of a compound in combination with a pharmaceutically acceptable carrier selected from the group consisting of a slow release carrier, an implant and a transdermal patch, said compound being a member of a group having the formula:

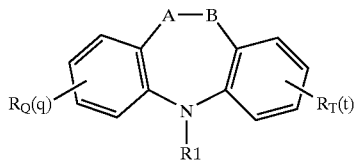

wherein,

A is CH, $CR_2R_3$, or C=Q; B is CH, $CR_4R_5$ or $NR_6$, wherein $R_2$, $R_3$, $R_4$, $R_5$ and $R_6$ are each independently selected from the group consisting of hydrogen, halogen, hydroxyl, saturated, unsaturated, aliphatic, or branched alkyl, substituted or unsubstituted $(CH_2)_m$-(hetero)aryl; or A and B together are C=C; $R_1$ is an unsaturated alkyl, amino-alcohol, cycloalkyl, and $C(=O)(CH_2)_n NR'R''$, $(CH_2)_n CHOHCH_2 NR'R''$, wherein n is an integer being 0–5; $R_Q$, $R_T$, R', and R" are each independently a hydrogen, halogen, hydroxyl, saturated, unsaturated, aliphatic, or branched alkyl, substituted or unsubstituted $(CH_2)_m$-(hetero)aryl, m being 0–5 and sulfonylamide; q and t are each an integer independently selected from 1–4, and pharmaceutically acceptable salts thereof.

7. The composition of claim 6, wherein A and B are each a carbon, $R_2$, $R_3$, $R_4$ and $R_5$ are each a hydrogen, and $R_1$ is $C(=O)(CH_2)_n NR'R''$, n being 0–5, R' and R are each hydrogen and R" is as defined above.

8. The composition of claim 7, wherein n is 1 and or 2 and R" is an alkyl selected from the group consisting of methyl, ethyl, propyl, iso-propyl, n-butyl, and tert-butyl.

9. The composition of claim 7, wherein n is 1 and or 2 and R" is saturated or unsaturated $(CH_2)_m$-cycloalkyl or $(CH_2)_m$-(hetero)aryl, m being 0–5.

10. The composition of claim 7, wherein m is 1 and R" is an aromatic 6-member ring.

11. The composition of claim 6, wherein n is 2 and R" is an alkyl selected from the group consisting of ethyl, propyl, n-butyl, iso-butyl, tert-butyl and sec-butyl.

12. The composition of claim 6, wherein n is 2 and R" is saturated or unsaturated $(CH_2)_m$-(hetero)aryl, m being 0–5.

13. The compound of claim 6, wherein said R1 is in a form selected from the group consisting of an R enantiomeric form, an S enantiomeric form, and a racemic mixture thereof.

14. A method for treating arrhythmia in a subject, the method comprising the step of administering a pharmaceutically effective amount of a compound, said compound being a member of a group having the formula:

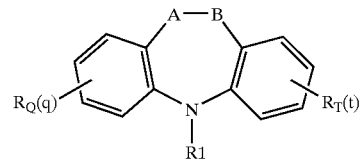

wherein,

A is CH, $CR_2R_3$, or C=Q; B is CH, $CR_4R_5$ or $NR_6$, wherein $R_2$, $R_3$, $R_4$, $R_5$ and $R_6$ are each independently selected from the group consisting of hydrogen, halogen, hydroxyl, saturated, unsaturated, aliphatic, or branched alkyl, substituted or unsubstituted $(CH_2)_m$-(hetero)aryl; or A and B together are C=C; $R_1$ is an unsaturated alkyl, amino-alcohol, cycloalkyl, and $C(=O)(CH_2)_m NR'R''$, $(CH_2)_n CHOHCH_2 NR'R''$, wherein n is an integer being 0–5; $R_Q$, $R_T$, R', and R" are each independently a hydrogen, halogen, hydroxyl, saturated, unsaturated, aliphatic, or branched alkyl, substituted or unsubstituted $(CH_2)_m$-(hetero)aryl, m being 0–5 and sulfonylamide; q and t are each an integer independently selected from 1–4, and pharmaceutically acceptable salts thereof.

15. The method of claim 14, wherein A and 6 are each a CH moiety, $R_2$, $R_3$, $R_4$ and $R_5$ are each a hydrogen, and $R_1$ is $C(=O)(CH_2)_n NR'R''$, n being 0–5, R and R' are each hydrogen and R" is as defined above.

16. The method of claim 14, wherein n is 2 and R" is an alkyl selected from the group consisting of methyl, ethyl, propyl, iso-propyl, n-butyl, iso-butyl, tert-butyl and sec-butyl.

17. The method of claim 15, wherein n is 2 and R" is saturated or unsaturated $(CH_2)_m$-(hetero)aryl, m being 0–5.

18. The method of claim 14, wherein n is 2 and R" is an alkyl selected from the group consisting of methyl, ethyl, propyl, iso-propyl, n-butyl, and tert-butyl.

19. The method of claim 14, wherein n is 2 and R" is saturated or unsaturated $(CH_2)_m$-(hetero)aryl, m being 0–5.

20. The method of claim 15, wherein said compound is administered to the subject parenterally.

21. The method of claim 15, wherein an implanted defibrillator is implanted is the subject, such that said compound is an adjunct treatment to defibrillation by said implanted defibrillator.

22. The compound of claim 14, wherein said R1 is in a form selected from the group consisting of an R enantiomeric form, an S enantiomeric form, and a racemic mixture thereof.

23. A method for treating ventricular fibrillation in a subject, the method comprising the step of administering a pharmaceutically effective amount of a compound, said compound being a member of a group having the formula:

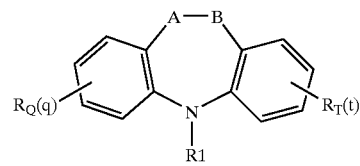

wherein,

A is CH, or CR$_2$R$_3$, B is CH, CR$_4$R$_5$ or NR$_6$, wherein R$_2$, R$_3$, R$_4$, R$_5$ and R$_6$ are each independently selected from the group consisting of hydrogen, halogen, hydroxyl, saturated, unsaturated, aliphatic, or branched alkyl, substituted or unsubstituted (CH$_2$)$_m$-(hetero)aryl; or A and B together are C=C; R$_1$ is an unsaturated alkyl, amino-alcohol, cycloalkyl, and C(=O)(CH$_2$)$_m$NR'R", (CH$_2$)$_n$CHOHCH$_2$NR'R", wherein n is an integer being 0–5; R$_Q$, R$_T$, R', and R" are each independently a hydrogen, halogen, hydroxyl, saturated, unsaturated, aliphatic, or branched alkyl, substituted or unsubstituted (CH$_2$)$_m$-(hetero)aryl, m being 0–5 and sulfonylamide; q and t are each an integer independently selected from 1–4; and pharmaceutically acceptable salts thereof.

24. The method of claim 23, wherein A and 6 are each a CH moiety, R$_2$, R$_3$, R$_4$ and R$_5$ are each a hydrogen, and R$_1$ is C(=O)(CH$_2$)$_n$NR'R", n being 0–5, R and R' are each hydrogen and R" is as defined above.

25. The method of claim 24, wherein n is 2 and R" is an alkyl selected from the group consisting of methyl, ethyl, propyl, iso-propyl, n-butyl, and tert-butyl.

26. The method of claim 24, wherein n is 2 and R" is saturated or unsaturated (CH$_2$)$_m$-(hetero)aryl, m being 0–5.

27. The method of claim 23, wherein A and is CR$_2$, R$_3$ and B is CR$_4$, R$_5$, R2, R$_3$, R$_4$, R$_5$ and R$_6$ are each a hydrogen, and R$_1$ is C(=O)(CH$_2$)$_n$NR'R", n being 0–5 and R' is a hydrogen and R" is as defined above.

28. The composition of claim 27, wherein n is 2 and R" is an alkyl selected from the group consisting of ethyl, propyl, iso-propyl, n-butyl, iso butyl, tert-butyl and sec-butyl.

29. The composition of claim 27, wherein n is 2 and R" is saturated or unsaturated (CH$_2$)$_m$-(hetero)aryl, m being 0–5.

30. The method of claim 23, wherein said compound is administered to the subject parenterally.

31. The method of claim 23, wherein an implanted defibrillator is implanted is the subject, such that said compound is an adjunct treatment to defibrillation by said implanted defibrillator.

32. The compound of claim 6, wherein said R1 is in a form selected from the group consisting of an R enantiomeric form, an S enantiomeric form, and a racemic mixture thereof.

33. A method of treating cardiac ischernis in a subject comprising the step of administering to the subject a composition comprising a pharmaceutically effective amount of a compound in combination with a pharmaceutically acceptable carrier, said compound being a member of a group having the formula:

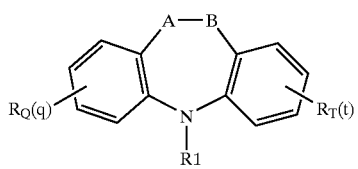

wherein A is CH, or CR$_2$R$_3$; B is CH, CR$_4$R$_5$ or NR$_6$, wherein R$_2$, R$_3$, R$_4$, R$_5$ and R$_6$ are each independently selected from the group consisting of hydrogen, halogen, hydroxyl, saturated, unsaturated, aliphatic, or branched alkyl, substituted or unsubstituted (CH$_2$)$_m$-(hetero)aryl; m being 0–5 or A and B together are C=C; R$_1$ is saturated or unsaturated alkyl, amino-alcohol, cycloalkyl, and C(=O)(CH$_2$)$_m$NR'R", (CH$_2$)$_n$CHOHCH$_2$NR'R", wherein n is an integer being 0–5; R$_Q$, R$_T$, R', and R" are each independently a hydrogen, halogen, hydroxyl, saturated, unsaturated, aliphatic, or branched alkyl, substituted or unsubstituted (CH$_2$)$_m$-(hetero)aryl, and sulfonylamide; q and t are each an integer independently selected from 1–4; and pharmaceutically acceptable salts thereof.

34. The method of claim 33, wherein the step of said composition to the subject further comprises the steps of:
(i) applying the composition to an implant; and
(ii) insetting said implant into said tissue of the subject.

35. The compound of claim 33, wherein said R1 is in a form selected from the group consisting of an R enantiomeric form, an S enantiomeric form, and a racemic mixture thereof.

36. A method for transforming sustained ventricular fibrillation to spontaneously defibrillating transient ventricular fibrillation in a subject, the method comprising the step of inducing cardiac sympathetic activity by administering a compound to the subject, said compound being a member of a group having the formula:

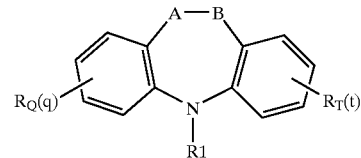

wherein
A is CH, or CR$_2$R$_3$; B is CH, CR$_4$R$_5$ or NR$_6$, wherein R$_2$, R$_3$, R$_4$, R$_5$ and R$_6$ are each independently selected from the group consisting of hydrogen, halogen, hydroxyl, saturated, unsaturated, aliphatic, or branched alkyl, substituted or unsubstituted (CH$_2$)$_m$-(hetero)aryl; m being 0–5 or A and B together are C=C; R$_1$ is saturated or unsaturated alkyl, amino-alcohol, cycloalkyl, and C(=O)(CH$_2$)$_m$NR'R", (CH$_2$)$_n$CHOHCH$_2$NR'R", wherein n is an integer being 0–5; R$_Q$, R$_T$, R', and R" are each independently a hydrogen, halogen, hydroxyl, saturated, unsaturated, aliphatic, or branched alkyl, substituted or unsubstituted (CH$_2$)$_m$-(hetero)aryl, and sulfonylamide; q and t are each an integer independently selected from 1–4; and pharmaceutically acceptable salts thereof.

37. The method of claim 36, wherein A and 6 are each a CH moiety, R$_2$, R$_3$, R$_4$ and R$_5$ are each a hydrogen, and R$_1$ is C(=O)(CH$_2$)$_n$NR'R", n being 0–5, R and R' are each hydrogen and R" is as defined above.

38. The method of claim 37, wherein n is 2 and R" is an alkyl selected from the group consisting of methyl, ethyl, propyl, iso-propyl, n-butyl, iso-butyl, tert-butyl and sec-butyl.

39. The method of claim 37, wherein n is 2 and R" is saturated or unsaturated (CH$_2$)$_m$-(hetero)aryl, m being 0–5.

40. The method of claim 36, wherein A is CR$_2$R$_3$ and B is CR$_4$R$_5$, R$_2$, R$_3$, R$_4$, R$_5$ and R$_6$ are each a hydrogen, and R$_1$ is C(=O)(CH$_2$)$_n$NR'R", n being 0–5, R' is a hydrogen and R" is as defined above.

41. The composition of claim 40, wherein n is 2 and R" is an alkyl selected from the group consisting of methyl, ethyl, propyl, iso-propyl, n-butyl, and tert-butyl.

42. The composition of claim 40, wherein n is 2 and R" is saturated or unsaturated (CH$_2$)$_m$-(hetero)aryl, m being 0–5.

43. The compound of claim 36, wherein said R1 is in a form selected from the group consisting of an R enantiomeric form, an S enantiomeric form, and a racemic mixture thereof.

* * * * *

UNITED STATES PATENT AND TRADEMARK OFFICE
CERTIFICATE OF CORRECTION

PATENT NO. : 6,908,915 B1  
APPLICATION NO. : 10/069455  
DATED : June 21, 2005  
INVENTOR(S) : Mordechai Erez et al.

Page 1 of 1

It is certified that error appears in the above-identified patent and that said Letters Patent is hereby corrected as shown below:

<u>On the cover sheet</u>:

Please insert: [30]  Foreign Application Priority Data

Sep. 1, 1999   (IL)   Israel ..........................131685

<u>In the Claims</u>:

Claim 33 at Column 23, Line 43, correct "ischernis" to -- ischemia --

Signed and Sealed this

Twentieth Day of May, 2008

JON W. DUDAS  
*Director of the United States Patent and Trademark Office*